United States Patent [19]

Küppers et al.

[11] 4,203,997

[45] May 20, 1980

[54] DIRECTLY-PRESSABLE ASCORBIC ACID-CONTAINING GRANULATES

[75] Inventors: Walter Küppers, Reinheim; Pasquale Della Mura, Darmstadt, both of Fed. Rep. of Germany

[73] Assignee: Merck Patent Gesellschaft mit Beschränkter Haftung, Darmstadt, Fed. Rep. of Germany

[21] Appl. No.: 878,362

[22] Filed: Feb. 16, 1978

[30] Foreign Application Priority Data

Feb. 17, 1977 [DE] Fed. Rep. of Germany ....... 2706660

[51] Int. Cl.² ............................................ A61K 31/365
[52] U.S. Cl. ..................................................... 424/280
[58] Field of Search ......................................... 424/280

[56] References Cited

U.S. PATENT DOCUMENTS

| | | | |
|---|---|---|---|
| 3,200,039 | 8/1965 | Thompson | 424/280 |
| 3,247,065 | 4/1966 | Koff | 424/280 |
| 3,384,546 | 5/1968 | Palermo | 424/280 |
| 3,446,894 | 5/1969 | Magid | 424/280 |
| 3,453,368 | 7/1969 | Magid | 424/280 |
| 3,873,713 | 3/1975 | Haas et al. | 424/280 |
| 4,036,948 | 7/1977 | Kitamori et al. | 424/280 |

OTHER PUBLICATIONS

Am. Pharmacy (1947)–Lyman (ed.), pp. 218–219.
Remington's Pharmaceutical Sciences 13th Ed., p. 1407–(1965).
Vitamin C:Its Molecular Biology and Medical Potential–Lewin–Academic Press, N.Y.–p. 16 (1976).

*Primary Examiner*—Douglas W. Robinson
*Attorney, Agent, or Firm*—Millen & White

[57] ABSTRACT

An ascorbic acid granulate comprising 90–93 wt. % of ascorbic acid, 5–9 wt. % of a sugar or sugar alcohol and about 1–2 wt. % of a lubricant may be directly compressed.

11 Claims, No Drawings

DIRECTLY-PRESSABLE ASCORBIC ACID-CONTAINING GRANULATES

BACKGROUND OF THE INVENTION

The present invention relates to solid, directly-pressable ascorbic acid granulates, processes for their preparation and their use. Such granulates can be used for the preparation of ascorbic acid-containing, solid compositions which contain ascorbic acid as the sole active material or in which ascorbic acid is present as an additive to other adjuvant/active material mixtures.

Ascorbic acid is obtainable not only in crystallized but also in powder form. Both forms are, per se, not directly-pressable, but rather more or less large amounts of adjuvant and additional materials are necessary. Moreover, in order to achieve satisfactory control of the properties of such solid compositions, such as disintegration properties, hardness, mechanical and chemical stability, coloration etc., as a rule, additional materials are needed. However, since ascorbic acid is generally administered in relatively large dosage units, e.g. 500 mg or even 1 g, the addition of large amounts of adjuvant materials leads to undesirably large dosage forms of the compositions.

in the past, granulates and compositions which possess a very high content of ascorbic acid and, nevertheless, display satisfactory properties, have been prepared. Such compositions are described e.g., in the U.S. Pat. Nos. 3,293,132 and G.B. Pat. No. 1,109,186. However, these compositions and the processes for their preparation display some significant disadvantages. Thus, in U.S. Pat. No. 3,293,132, a spray drying process is used, for which powdered ascorbic acid exclusively can be employed. In G.B. Pat. No. 1,109,186, the process requires a starting material of a crystalline ascorbic acid with a precisely defined particle size distribution. In this patent, it is stated that good results cannot be achieved with powdered ascorbic acid or with crystalline ascorbic acid not possessing the narrowly-limited particle size distribution. Finally, in the case of both Patents, the granulates obtained can in no way be directly pressed but rather must be mixed, in a further process step, with additional additives before, e.g., tablets can be pressed therefrom.

In U.S. Pat. No. 3,446,894, ascorbic acid granulates and tablets which possess a content of at least 70 or even 85% ascorbic acid are disclosed. In the Examples, tablets are described with 74.3 and 87.6% ascorbic acid. Compositions with a higher content of ascorbic acid are thus not obtainable. It also follows from the Examples and the patent claims therein that a whole series of adjuvant and additive materials are necessary in order to obtain a stable granulate which then, also again in an additional process step, must be mixed with even more adjuvant agents in order to press tablets therefrom.

SUMMARY OF THE INVENTION

Thus, it is an object of this invention to provide ascorbic acid-containing granulates which possess a very high content of ascorbic acid and are directly-pressable without further additives.

It is another object of this invention to provide such granulates whose preparation does not require a special ascorbic acid, molecular form (e.g., powder or crystalline).

It is still another object of this invention to provide such granulates which are suitable for the production of solid, ascorbic acid-containing compositions which have good mechanical and chemical stability, good disintegration properties and sufficient hardness and, in particular, also show no discoloration even after comparatively long storage.

It is a further object of this invention to provide such granulates whose production is simple and requires as small a number of materials as possible.

Upon further study of the specification and appended claims, further objects and advantages of this invention will become apparent to those skilled in the art.

These objects of this invention have been attained by providing, in a composition aspect, solid, directly-pressable ascorbic acid granulates comprising 90–93 weight % of ascorbic acid, 5–9 weight % of a sugar or sugar alcohol and about 1–2 weight % of a lubricant.

In a method aspect, this invention provides a method of producing tablets of ascorbic acid which comprises directly compressing a granulate comprising 90–93 weight % of ascorbic acid, 5–9 weight % of a sugar or sugar alcohol and 1–2 weight % of a lubricant.

In another method aspect, this invention relates to a method of directly compressing a granulate of ascorbic acid which comprises employing as the granulate a mixture comprising 90–93 weight % of ascorbic acid, 5–9 weight % of a sugar or a sugar alcohol and 1–2 weight % of a lubricant.

In another composition aspect, this invention relates to a granulate comprising 90–93 weight % of ascorbic acid, 5–9 weight % of a sugar or sugar alcohol and 1–2 weight % of a lubricant which has been directly pressed.

In still another composition aspect, this invention relates to a granulate comprising 90–93 weight parts of ascorbic acid and 5–9 weight parts of a sugar or a sugar alcohol.

In still another method aspect this invention relates to a process for the production of directly pressable ascorbic acid granulates wherein an at least partly granulated base mixture of 90–93 parts by weight of ascorbic acid and 5–9 parts by weight of a sugar or sugar alcohol is mixed with 1–2 parts by weight of a lubricant.

DETAILED DISCUSSION

Surprisingly, it has been found that granulates containing 90–93 weight % of ascorbic acid, 5–9 weight % of a sugar or of a sugar alcohol and about 1–2 weight % of a lubricant, can be pressed directly, without further additives, to produce qualitatively satisfactory, solid, ascorbic acid-containing compositions, and that such good results are obtained irrespective of whether powdered or crystalline ascorbic acid is used as the starting material.

The term "direct compression" has its conventional meaning herein, i.e., it refers to the pressing of a substance or mixture directly without any pretreatments such as pre-pressing or wetting, etc., which are generally required for most pharmaceutical formulations. The method is fully described, for example, in Hagers Handbuch der Pharmazeutischen Praxis, Vol. VII, Springer-Verlag 1971, whose disclosure is incorporated by reference herein.

The granulates of this invention, in particular, have the advantage that, without further additives, and without additional process steps, they can be pressed directly into tablets or other solid compositions and that such production occurs in a simple and economical way with conventional machinery. The quality of the granulates according to this invention is, astonishingly, independent of the use of pulverized or crystalline ascorbic acid. Thus, there is no limitation on the use of ascorbic acid of any particular shape or crystalline size.

The production of the granulates according to this invention is preferably carried out so that an at least partly granulated base mixture is produced consisting solely of ascorbic acid and a sugar or sugar alcohol. This at least partially granulated base mixture can be produced in various forms. Thus, it is possible, e.g., surprisingly by moistening, granulating and drying of pure ascorbic acid, to first produce a sufficiently solid granulate with a particle size of about 40 to about 1000 μm. By mixing this granulate with about the same amount of crystalline ascorbic acid and a proportionate amount of the sugar or sugar alcohol per the requirement of this invention, a base mixture is attained. This base mixture of 91-95 weight % of ascorbic acid, preferably 91-92 weight % of ascorbic acid, and 5-9 weight % of sugar or a sugar alcohol, preferably 8-9 weight % thereof, should have an average particle size of about 0.1-2 mm, the same as the final granulate. The water content of the dry base mixture is a maximum of 0.1 weight %. By subsequent admixing of the lubricant, the pressable ascorbic acid granulate according to this invention can be produced.

However, the base mixture can also be produced by mixing appropriate amounts of the ascorbic acid with the sugar or sugar alcohol, moistening with about 6-10 weight % of water, passing this mass through a compactor and drying. The relative proportions of ingredients and the amount of water in the dried product is as described above. The "briquets" thereby obtained are comminuted and, after admixture of the lubricant, the pressable ascorbic acid granulate according to this invention is produced.

Although not as industrially attractive as the foregoing procedure, other orders of mixing, of course, can be utilized to prepare the granulate of this invention. Thus, all these components can be mixed together at once or any of the three can be added to a mixture of the other two. No matter which mixing technique is used, the final water content of the granulate should not exceed 0.1 weight % and the average particle size 0.1-2 mm. The ascorbic acid employed as a starting material may be all crystalline form or all powder form or a mixture of the two in any convenient proportions.

Surprisingly, for these production processes, only a minimum amount of adjuvant and additional materials is required. Thus, astonishingly, no further binding agent is necessary in addition to the sugar or sugar alcohol. Thus, the addition of a conventional binding agent, such as, e.g., starch, methyl cellulose or the like, can be completely omitted.

Suitable sugars include all conventional sugars, such as, e.g., glucose, mannose, fructose, etc., but cane sugar (saccharose) is preferred. However, there can advantageously also be employed conventional sugar alcohols, such as, e.g., sorbitol, mannitol, xylitol, whereby sorbitol is preferred.

The sugar or sugar alcohol is employed in an amount of 5-9 weight %. Very good results are achieved even with the smallest amount in this range. However, the sugar or sugar alcohol is preferably employed in an amount of 8-9 weight %.

The particle size of the granulates according to the invention is, in itself, not critical. However, as a rule, granulates are employed with an average particle size of 0.1 to 2 mm, those with a particle size of 0.1 to 1 mm, being especially preferred.

In any case, the so produced granulates can be directly pressed into tablets without further need for any other additives. As a result, it is surprising that a very good pressability is achieved even with the very small amounts of 1-2 weight % of lubricant.

Suitable lubricants, in principle, include all conventional lubricants. For example, fatty acid mono-, di- or triglycerides or alkali or alkaline earth metal salts of fatty alcohol sulphates are suitable. Preferably, e.g., glycerol monostearate, magnesium lauryl sulphate, magnesium stearate, stearic acid or glycerol trifatty acid esters (of palmitic or stearic acid) are used.

After the mixing and sieving operations, the granulates of this invention are fully capable of use in tablet production. They are characterized by excellent flowability, color stability, galenical and chemical storage stability and very good miscibility. Using them, tablets, dragees or capsules can be produced directly, or, by admixture of additional active material/adjuvant material mixtures, other ascorbic acid-containing, solid compositions can be produced. Such other adjuvants are fully conventional and need only be pharmaceutically acceptable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The ascorbic acid base granulate used in Examples 1-8 can be produced in the following way.

100 parts by weight of ascorbic acid, particle size below 250 μm, are well moistened with 15 parts by weight of water, granulated and dried. The so-obtained ascorbic acid base granulate contains about 99.9% of ascorbic acid and a maximum of 0.1% water.

EXAMPLE 1

To 45 parts of ascorbic acid base granulate are added 45 parts of crystallized ascorbic acid, 9 parts of sorbitol and 1 part of magnesium stearate and the resultant mixture is well mixed. The so-obtained ascorbic acid granulate can be pressed directly.

EXAMPLE 2

Example 1 is repeated except that cane sugar is employed instead of sorbitol.

EXAMPLE 3

Example 1 is repeated except that mannitol is used instead of sorbitol.

EXAMPLE 4

Example 1 is repeated except that xylitol is used instead of sorbitol.

EXAMPLE 5

To 45 parts of ascorbic acid base granulate are added 45 parts of crystallized ascorbic acid, 8 parts of sorbitol and 2 parts of glycerol monostearate and the resultant mixture is well mixed. The so-obtained ascorbic acid granulate can be pressed directly.

EXAMPLE 6

Example 5 is repeated except that mannitol is used instead of sorbitol.

EXAMPLE 7

Example 5 is repeated except that xylitol is used instead of sorbitol.

EXAMPLE 8

Example 5 is repeated except that cane sugar is used instead of sorbitol.

EXAMPLE 9

A mixture of 90 parts ascorbic acid and 8 parts of sorbitol is moistened through with 8 parts of water, passed through a compactor, dried and comminuted. By admixing 2 parts of magnesium stearate, a directly pressable ascorbic acid granulate is obtained.

EXAMPLE 10

Example 9 is repeated except that mannitol is used instead of sorbitol.

EXAMPLE 11

Example 9 is repeated except that xylitol is used instead of sorbitol.

EXAMPLE 12

Example 9 is repeated except that cane sugar is used instead of sorbitol.

EXAMPLE 13

A mixture of 90 parts of ascorbic acid and 9 parts of sorbitol is moistened through with 8 parts of water, passed through a compactor, dried and comminuted. By admixing 1 part of magnesium stearate, a directly pressable ascorbic acid granulate is obtained.

EXAMPLE 14

Example 13 is repeated except that mannitol is used instead of sorbitol.

EXAMPLE 15

Example 13 is repeated except that xylitol is used instead of sorbitol.

EXAMPLE 16

Example 13 is repeated except that cane sugar is used instead of sorbitol.

The preceding examples can be repeated with similar success by substituting the generically or specifically described reactants and/or operating conditions of this invention for those used in the preceding examples.

From the foregoing description, one skilled in the art can easily ascertain the essential the characteristics of this invention, and without departing from the spirit and scope thereof, can make various changes and modifications of the invention to adapt it to various usages and conditions.

What is claimed is:

1. In a directly pressable granulate comprising 90–93 weight % of ascorbic acid and a binder, the improvement wherein the binder consists essentially of, sorbitol, mannitol or xylitol.

2. The granulate of claim 1 wherein the amount of sugar or sugar alcohol binder is 5–9 weight %.

3. The granulate of claim 1, wherein the average particle size is 0.1–2 mm.

4. The compressed product produced by pressing the granulate of claim 1.

5. The directly pressable ascorbic acid granulate of claim 1 comprising 90–93 weight % of ascorbic acid, 5–9 weight % of a sugar or sugar alcohol binder and about 1–2 weight % of a lubricant.

6. The granulate of claim 1 which consists essentially of 90–93 weight % of ascorbic acid, 5–9 weight % of a sugar or sugar alcohol and about 1–2 weight % of a lubricant.

7. The compressed product produced by pressing the granulate of claim 6.

8. The granulate of claim 1, wherein 8–9 weight % of sugar or sugar alcohol is contained.

9. The granulate of claim 8, which contains 90 weight % of ascorbic acid, 8–9 weight % of sorbitol and 1–2 weight % of a lubricant.

10. The granulate of claim 1 which further comprises from 1–2 weight % of a different ingredient which functions as a lubricant.

11. In a directly compressible ascorbic acid granulate consisting essentially of ascorbic acid and a binder the improvement wherein the sole binder is 5–9 weight % of sugar, sorbitol, mannitol or xylitol and the amount of ascorbic acid is 90–93 weight %.

* * * * *

UNITED STATES PATENT AND TRADEMARK OFFICE
CERTIFICATE OF CORRECTION

PATENT NO. : 4,203,997
DATED : May 20, 1980
INVENTOR(S) : Walter Kuppers et al

It is certified that error appears in the above-identified patent and that said Letters Patent are hereby corrected as shown below:

Column 6, lines 18-19: reads "wherein the binder consists essentially of, sorbitol, mannitol or xylitol."
should read -- wherein the binder consists essentially of sugar, sorbitol, mannitol or xylitol. --

Signed and Sealed this

Twenty-sixth Day of August 1980

[SEAL]

Attest:

SIDNEY A. DIAMOND

Attesting Officer

Commissioner of Patents and Trademarks